(12) United States Patent
Nakasuji et al.

(10) Patent No.: US 7,479,634 B2
(45) Date of Patent: *Jan. 20, 2009

(54) ELECTRON BEAM APPARATUS AND DEVICE MANUFACTURING METHOD USING THE SAME

(75) Inventors: Mamoru Nakasuji, Yokohama (JP); Takao Kato, Shibuya-ku (JP); Kenji Watanabe, Fujisawa (JP); Shoji Yoshikawa, Hachioji (JP); Tohru Satake, Chigasaki (JP); Nobuharu Noji, Zushi (JP)

(73) Assignee: Ebara Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/714,130

(22) Filed: Mar. 6, 2007

(65) Prior Publication Data

US 2007/0158565 A1 Jul. 12, 2007

Related U.S. Application Data

(62) Division of application No. 11/262,844, filed on Nov. 1, 2005, now Pat. No. 7,205,540, which is a division of application No. 10/234,152, filed on Sep. 5, 2002, now Pat. No. 6,998,611.

(30) Foreign Application Priority Data

| Sep. 6, 2001 | (JP) | ............................ 2001-269880 |
| Sep. 10, 2001 | (JP) | ............................ 2001-273078 |
| Dec. 3, 2001 | (JP) | ............................ 2001-368960 |

(51) Int. Cl.
*G21K 7/00* (2006.01)
*G21G 4/00* (2006.01)
*G01N 23/00* (2006.01)

(52) U.S. Cl. ..................... 250/310; 250/311; 250/492.3

(58) Field of Classification Search ................. 250/310, 250/306, 307, 311, 396 R, 396 ML, 397, 250/398, 492.1, 492.2, 492.3
See application file for complete search history.

(56) References Cited

U.S. PATENT DOCUMENTS 4,515,858 A    5/1985 Bayan
(Continued)

FOREIGN PATENT DOCUMENTS

JP    62-119849 A    6/1987
(Continued)

OTHER PUBLICATIONS

Thompson et al., "Fluctuations in Space-charged-limited Current at Moderately high Frequencies", RCE Review, vol. 4, 1940, pp. 441-472.
(Continued)

*Primary Examiner*—Bernard E Souw
(74) *Attorney, Agent, or Firm*—Westerman, Hattori, Daniels & Adrian, LLP.

(57) ABSTRACT

An electron beam apparatus is provided for reliably measuring a potential contrast and the like at a high throughput in a simple structure. The electron beam apparatus for irradiating a sample, such as a wafer, formed with a pattern with an electron beam to evaluate the sample comprises an electron-optical column for accommodating an electron beam source, an objective lens, an E×B separator, and a secondary electron beam detector; a stage for holding the sample, and relatively moving the sample with respect to the electron-optical column; a working chamber for accommodating the stage and capable of controlling the interior thereof in a vacuum atmosphere; a loader for supplying a sample to the stage; a voltage applying mechanism for applying a voltage to the sample, and capable of applying at least two voltages to a lower electrode of the objective lens; and an alignment mechanism for measuring a direction in which dies are arranged on the sample. When the sample is evaluated, a direction in which the stage is moved is corrected to align with the direction in which the dies are arranged.

7 Claims, 11 Drawing Sheets

U.S. PATENT DOCUMENTS

| | | | |
|---|---|---|---|
| 4,516,253 A | 5/1985 | Novak | |
| 5,276,331 A | 1/1994 | Oae et al. | |
| 5,283,440 A | 2/1994 | Sohda et al. | |
| 6,087,667 A | 7/2000 | Nakasuji et al. | |
| 6,515,296 B1 | 2/2003 | Komatsu et al. | |
| 6,522,519 B1 | 2/2003 | Hirayanagi | |
| 6,559,663 B2 | 5/2003 | Shinada et al. | |
| 6,583,426 B1 | 6/2003 | Kawanami et al. | |
| 6,586,952 B2 | 7/2003 | Nozoe et al. | |
| 6,593,152 B2 | 7/2003 | Nakasuji et al. | |
| 6,593,686 B1 | 7/2003 | Yui | |
| 6,855,929 B2 | 2/2005 | Nakasuji et al. | |
| 6,998,611 B2 * | 2/2006 | Nakasuji et al. | 250/310 |
| 7,005,641 B2 * | 2/2006 | Nakasuji et al. | 250/310 |
| 7,012,251 B2 | 3/2006 | Nakasuji et al. | |
| 7,205,540 B2 * | 4/2007 | Nakasuji et al. | 250/310 |
| 2002/0028399 A1 | 3/2002 | Nakasuji et al. | |
| 2002/0036264 A1 | 3/2002 | Nakasuji et al. | |
| 2002/0088940 A1 | 7/2002 | Watanabe et al. | |
| 2002/0109090 A1 | 8/2002 | Nakasuji et al. | |
| 2002/0130262 A1 | 9/2002 | Nakasuji et al. | |
| 2002/0142496 A1 | 10/2002 | Nakasuji et al. | |
| 2002/0148961 A1 | 10/2002 | Nakasuji et al. | |
| 2003/0007677 A1 | 1/2003 | Hiroi et al. | |
| 2003/0042417 A1 | 3/2003 | Nakasuji et al. | |
| 2004/0119023 A1 * | 6/2004 | Nakasuji et al. | 250/396 R |
| 2004/0183013 A1 | 9/2004 | Nakasuji et al. | |
| 2005/0051724 A1 | 3/2005 | Nakasuji et al. | |
| 2005/0121611 A1 | 6/2005 | Kimba et al. | |
| 2006/0054819 A1 | 3/2006 | Nakasuji et al. | |
| 2006/0097200 A1 * | 5/2006 | Nakasuji et al. | 250/493.1 |
| 2006/0102838 A1 | 5/2006 | Nakasuji et al. | |
| 2007/0158565 A1 * | 7/2007 | Nakasuji et al. | 250/310 |

FOREIGN PATENT DOCUMENTS

| | | |
|---|---|---|
| JP | 01-84629 | 3/1989 |
| JP | 9-171791 A | 6/1997 |
| JP | 11-162384 A | 6/1999 |
| JP | 11-233060 A | 8/1999 |
| JP | 2000-021341 | 1/2000 |
| JP | 2000-040481 | 2/2000 |
| JP | 2000-040485 | 2/2000 |
| JP | 2001-144168 | 5/2001 |

OTHER PUBLICATIONS

Pfeiffer et al., "Advanced deflection concept for large area, high resolution e-beam lithography", J. Vac. Sci. Technol., vol. 19, No. 4, Nov./Dec. 1981, pp. 1058-1063.

Smith et al., "The Detection and Measurement of Infra-red Radiation", Oxford at the Clarendon Press, 1968, pp. 188-197.

"Communication Engineering Handbook", Maruzen, Jul. 10, 1957, pp. 470-472.

* cited by examiner

ELECTRON BEAM APPARATUS AND DEVICE MANUFACTURING METHOD USING THE SAME

This application is the division of the U.S. application Ser. No. 11/262,844 dated Nov. 1, 2005, which is the division of the U.S. application Ser. No. 10/234,152 dated Sep. 5, 2002, all of which are incorporated by reference.

BACKGROUND OF THE INVENTION

The present invention relates to an electron beam apparatus for use with a wafer having patterns with a minimum line width of 0.1 micron or less for evaluating the wafer in a defect test, a line width measurement, an alignment accuracy measurement, and the like, and to a method of manufacturing devices with a high yield rate using the electron beam apparatus.

Conventionally, a defect detection, a CD measurement, a defect review, SEM, an alignment accuracy measurement, and the like have been conducted by known apparatuses which irradiate a sample such as a wafer with an electron beam to detect secondary electrons generated from the sample. Particularly, electron beams are widely used in a method of detecting defects of a sample by applying a charge to patterns on the sample, and measuring a resulting potential on the surface for the evaluation because such an evaluation cannot be performed on an optical basis.

For generating a potential contrast of a pattern on a sample in a conventional electron beam apparatus, it is known that an apparatus not provided with an energy filter for secondary electron beams has a low resolution, whereas an apparatus provided with such an energy filter can measure a potential with a low potential resolution. When the function of energy filter is given to an objective lens, a problem arises in that the resulting objective lens has a large aberration coefficient. Also, for correctly aligning a site of a sample under evaluation to the field of view of an electro-optical system, a sub-system is required for registration similar to a lithography system, giving rise to an additional problem that the overall apparatus is increased in size and complicated.

Additionally, in the conventional electron beam apparatus, a variety of problems have been left unsolved, for example, as follows:

(1) In regard to an E×B separator for separating a primary electron beam from a secondary electron beam, it is unknown how a desired accuracy is provided in a simple structure.

(2) Since the conventional electron beam apparatus involves large shot noise, a large beam current is required to provide a desired signal/noise ratio.

(3) There has been no electrostatic chuck which is capable of flatly chucking a convexly upwordly distorted wafer.

(4) In a region of a wafer in which a field of view of a primary optical system overlaps, some locations on the wafer could be dosed with an electron beam of intensity twice or four times higher, as the case may be, possibly giving rise to breakage of a gate oxidation layer of the wafer.

(5) The conventional electron beam apparatus experiences difficulties in ensuring a space near a lens located above an objective lens for disposing a deflector for scanning.

As has been known in the field of infrared detector, shot noise $i_f^2$ can be expressed by:

$$i_f^2 = 2e \cdot I_0 \cdot \Gamma^2 \cdot \Delta f$$

when a current $I_0$ is flowing through an electron gun. Under a condition in which an electron gun is operated under a temperature limited condition, $\Gamma$ is 1.0, while under a condition in which an electron gun is operated under space charge limited condition, $\Gamma$ is in a range from 0.1 to 1.0 (see R. A. Smith et al., "THE DETECTION AND MEASUREMENT OF INFRARED RADIATION," Oxford at the Clarendon Press, 1968, P195).

The shot noise $i_n^2$ as vacuum tube noise can be expressed by:

$$i_n^2 = \Gamma^2 \cdot 2e \cdot I_p \cdot B_f$$

where $i_n^2$=Square Value of Noise Current;
  e=Charge of Electron;
  $I_p$=Anode DC Current; and
  $B_f$=Frequency Band of Signal Amplifier;
  $\Gamma^2$ is a decreasing function of a cathode temperature $T_k$, and is measured as a value in a range of 0.16 to 0.018 (see "Communications Engineering Handbook" edited by Japanese Society of Electronic and Communications Engineers, p471 (1957)).

In regard to detection of signals by an electron beam apparatus, information on the infrared technologies and electron tube technologies as described above are not utilized in an effective way, and the shot noise is treated as $\Gamma$=1. In addition, although the shot noise can be reduced by increasing the cathode temperature of the electron gun, the cathode temperature is determined without taking into account the shot noise.

SUMMARY OF THE INVENTION

The present invention has been made to solve the variety of problems mentioned above, and it is an object of the invention to provide an electron beam apparatus in a simple structure which is capable of highly reliably making measurements of potential contrasts and the like with high throughput.

It is another object of the present invention to provide an electron beam apparatus which is capable or reducing shot noise to increase the S/N ratio, thereby detecting secondary electrons and the like emitted from a sample at a good S/N ratio by setting a cathode temperature in consideration of the shot noise.

It is a further object of the present invention to provide a device manufacturing method for evaluating a wafer in the middle of a process using the electron beam apparatus as described above to improve the yield rate.

To achieve the above object, according to a first aspect of the present invention, there is provided an electron beam apparatus for irradiating a sample, such as a wafer, formed with a pattern with an electron beam to evaluate the sample. The apparatus includes an electron-optical column for accommodating an electron beam source, an objective lens, an electromagnetic deflector, and a secondary electron beam detector; a stage for holding the sample, and relatively moving the sample with respect to the electron-optical column; a working chamber for accommodating the stage, and capable of controlling the interior thereof in a vacuum atmosphere; a loader for supplying the sample to the stage in the working chamber; a voltage applying mechanism for applying a voltage to the sample placed in the working chamber, wherein the wafer includes a plurality of small regions which are divided such that those regions do not overlap one another, and wherein only the small regions are subjected to an evaluation.

In the electron beam apparatus, the objective lens may be an electrostatic lens having at least three sheets of electrodes, and a central electrode of the three sheets of electrodes may have a thickness of 2 mm or less in an optical axial direction.

The electromagnetic deflector may include an octa-pole electrostatic deflector, and the electromagnetic deflector may be of a troidal type or a saddle type to form an E×B separator.

Preferably, the electron gun is operated under a space charge limited condition.

The electron beam apparatus further comprises an electrostatic chuck for fixing the sample on the stage, wherein the electrostatic chuck may include at least a first electrode comprising a central region and a portion of a peripheral region of the electrostatic chuck, and a second electrode comprising the rest of the peripheral region, and the second electrode may be applied with a voltage after the first electrode is applied with a voltage.

The electron beam apparatus may further comprise an alignment mechanism for measuring a direction in which dies are arranged on the sample, and the electron beam apparatus corrects a direction in which the stage is moved to align with the direction in which the dies are arranged when the sample is evaluated while the stage is continuously moved in a axial direction.

The objective lens is an electrostatic lens including at least three sheets of electrodes, wherein the focal distance of the objective lens is rapidly changed by changing a voltage applied to one of the at least three electrodes. The one electrode is a third electrode or an electrode located closer to the electron gun, of the at least three electrodes, counted from the sample.

Preferably, $0.9 < d/p < 1.2$ is satisfied, where p is a pixel dimension of the pattern, and d is a beam dimension of the electron beam irradiated to the pattern.

Preferably, the electrostatic deflector of the E×B separator is superposed with a scanning voltage to scan the sample.

The electron beam apparatus according to the first aspect of the present invention provides advantageous effects represented by the followings.

(1) The dimensions of the electrodes of the objective lens can be designed to provide a filtering effect for secondary electron beams and the axial chromatic aberration coefficient can be reduced.

(2) The throughput is not affected by registration because the registration can be performed in an extremely short time and even during an evaluation on a wafer.

(3) The E×B separator can be implemented for separating secondary electron beams from the primary optical system in a simple structure, and the aberration of the primary electron beam can be readily calculated.

(4) The shot noise can be reduced to 13% of a TFE electron gun.

(5) Even a convexly distorted wafer can be flatly chucked.

(6) Devices, particularly, gate oxide films are not susceptible to breakage.

(7) Dynamic focusing can be performed while an electrode of the objective lens is applied with a voltage close to a ground potential.

(8) The S/N ratio of the output from the secondary electron detector can be increased to a maximum value or a value close to that.

(9) The E×B separator and a scanning deflector can be located at optimal positions.

According to a second aspect of the present invention, there is provided an electron beam apparatus having an electron-optical column configured to irradiate a sample with an electron beam emitted from a thermal electron emitting cathode and focus one of secondary electrons emitted from the sample, reflected electrons, or absorbed electrons on a detection system, wherein the electron beam apparatus evaluates a signal to noise ratio in the detection system or a noise amount when the sample is irradiated with the electron beam while changing power for heating the thermal electron emitting cathode, to determine the power for heating the thermal electron emitting cathode.

Preferably, the power for heating the thermal electron emitting cathode is determined such that the signal to noise ratio exceeds a predetermined value or the noise amount is reduced to a predetermined value or less when a constant beam current is applied to a sample from the electron beam emitted from the thermal electron emitting cathode.

Preferably, the power for heating the thermal electron emitting cathode is determined such that an increasing ratio of the signal to noise ratio to the heating power is reduced to a predetermined value or less, or a decreasing rate of the noise amount is reduced to a predetermined value or less when a constant beam current is applied to a sample from the electron beam emitted from the thermal electron emitting cathode.

The power for heating the thermal electron emitting cathode may be determined by evaluating a ratio of a noise current to a beam current.

Preferably, the electron beam apparatus may roughly adjust the power for heating the thermal electron emitting cathode such that an electron gun current slowly changes when the power for heating the thermal electron emitting cathode is changed, and finely adjust the power for heating the thermal electron emitting cathode after the rough adjustment based on an evaluation on the signal to noise ratio in the detection system, or based on the noise amount.

The power for heating the thermal electron emitting cathode may be determined in consideration of a relationship between the power for heating the thermal electron emitting cathode and the signal to noise ratio, and a relationship between the power for heating the thermal electron emitting cathode and a lifetime of the thermal electron emitting cathode.

According to the second aspect of the present invention, the electron beam apparatus has an electro-optical column configured to irradiate a sample with an electron beam emitted from a thermal electron emitting cathode and focus one of secondary electrons emitted from the sample, reflected electrons or absorbed electrons on the detection system, wherein the electron beam apparatus evaluates a signal to noise ratio in the detection system or a noise amount when the sample is irradiated with the electron beam while changing power for heating the thermal electron emitting cathode, to determine the power for heating the thermal electron emitting cathode, so that the shot noise can be reduced to increase the S/N ratio, thereby making it possible to detect the secondary electrons emitted from the sample, or the like with a high S/N ratio.

According to a third aspect of the present invention, there is provided an electron beam apparatus which includes an electron gun having a thermal electron emitting cathode for emitting an electron beam; an aperture irradiated with the electron beam which is shaped by passing through the aperture, and projected onto a sample; an objective lens for generating an electric field for accelerating secondary electrons emitted from the sample; an E×B separator for introducing the secondary electrons to a secondary electron detector; and deflectors arranged at two stages and having deflection pivot at positions at which deflection chromatic aberration is minimized near the objective lens when the sample is scanned using the deflectors at two stages.

As a result of employing the foregoing configuration, the beam diameter is not increased even when the electron beam is deflected. In addition, a large beam current can be provided because a reduced image through the aperture is used as a beam.

The electron gun may operate under a space charge limited condition. The aperture may have a square shape. The sample is applied with a negative voltage, and a lower electrode of the objective lens may be applied with a voltage lower than the voltage applied to the sample.

Since the electron gun is operated under the space charge limited condition, the electron beam apparatus in the third embodiment can reduce the shot noise, satisfy the S/N ratio higher than 45, required for conducting a defect test and the like, eliminate the need for average summation, generate a sufficiently large signal in a single scanning session, and provide a beam for ensuring a resolution of 100 nm with the S/N ratio higher than 45.

Since the aperture is made in a square shape, a large beam current can be provided at a low brightness.

Since the sample is applied with a negative voltage, and the lower electrode of the objective lens is applied with a voltage lower than that applied to the sample, the potential contrast on the sample can be provided with a high S/N ratio.

According to a fourth aspect of the present invention, there is provided a device manufacturing method comprising the step of evaluating a wafer in the middle of a process or after completion of the process using a variety of electron beam apparatuses described above.

DETAILED DESCRIPTION OF THE INVENTION

Figure 1:
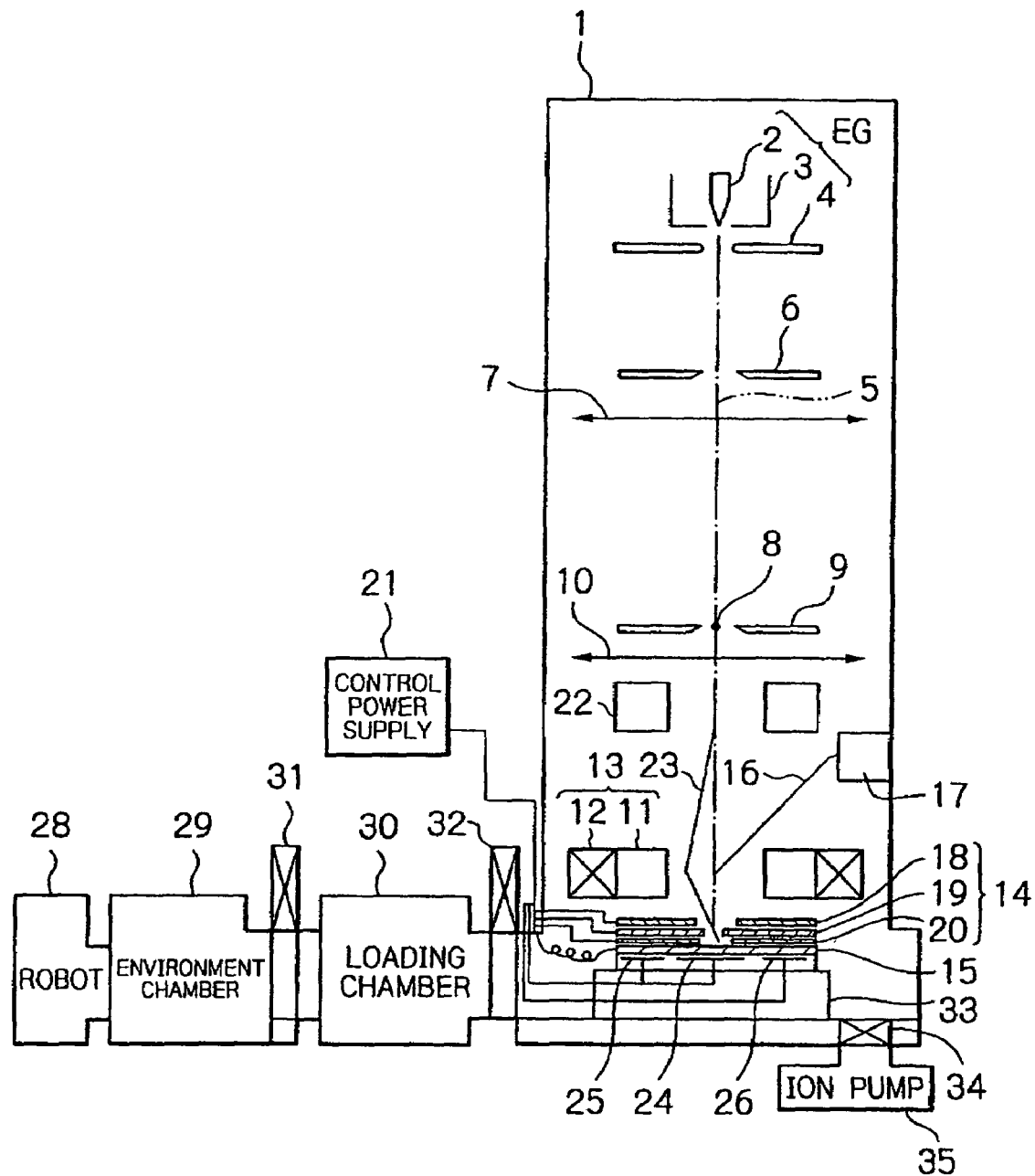
FIG. 1 is a diagram generally illustrating one embodiment of an electron beam apparatus according to the present invention.

FIG. 1 generally illustrates a first embodiment of an electron beam apparatus according to the present invention. In FIG. 1, an electron-optical column 1 contains an electron gun EG comprised of a cathode 2, a Wehnelt 3, and an anode 4. A primary electron beam emitted from the electron gun EG is irradiated to a first aperture plate 6 having an aperture formed in square on condition that a cross-over 5 is created between the first aperture plate 6 and a first condenser lens 7. In this manner, the primary electron beam that has passed through shaping aperture plate 6 is reduced by the first condenser lens 7 to form a cross-over image 8 on a circular aperture of a second aperture plate 9. The primary electron beam is further reduced by a second condenser lens 10, and passes through an ExB separator 13 made up of an electrostatic deflector 11 and an electromagnetic deflector 12. Then, the primary electron beam is converged by an objective lens 14, and a reduced image of the square aperture formed through the first aperture plate 6 is formed on a wafer 15.

Secondary electron beams emitted from the wafer 15 by the irradiation of the primary electron beam are accelerated and converged by the objective lens 14, and deflected by the ExB separator 13 to the right in FIG. 1 to take a trajectory 16, so that the secondary electron beams are detected by a secondary electron detector 17. The objective lens 14 has an upper electrode 18, a central electrode 19, and a lower electrode 20 which are applied with appropriate voltages from a control power supply 21.

The ExB separator 13 can be made up of, for example, an octa-pole electrostatic deflector and a saddle-type electromagnetic deflector in combination, so that it is advantageous in a simple structure and prevention of unwanted aberration for the primary electron beam. Here, the secondary electron beams can be detected depending on a particular scanning view, using only an electromagnetic deflector in place of the ExB separator.

For scanning the wafer 15 with the primary electron beam, the primary electron beam is controlled by the electrostatic deflector 11 and another electrostatic deflector 22 to travel along a trajectory 23. Since the electrostatic deflector 11 of the ExB separator 13 is used as the electrostatic deflector at the second stage, a space above the objective lens 14 can be utilized in an effective way. Moreover, considering that the electrostatic deflector at the second stage is advantageously located closer to the objective lens 14, the electrostatic deflector at the second stage can be placed at an optimal position by providing the electrostatic deflector 11 of the ExB separator 13 with a function of the electrostatic deflector at the second stage.

The wafer 15 is applied with a voltage of −4 kV from the control power supply 21. In this event, devices on the wafer 15 are susceptible to breakage unless the voltage from the control power supply 21 falls down, for example, at a rate of approximately 100 volts/10 seconds, so that the wafer 15 is gradually applied with the voltage.

Figure 2:
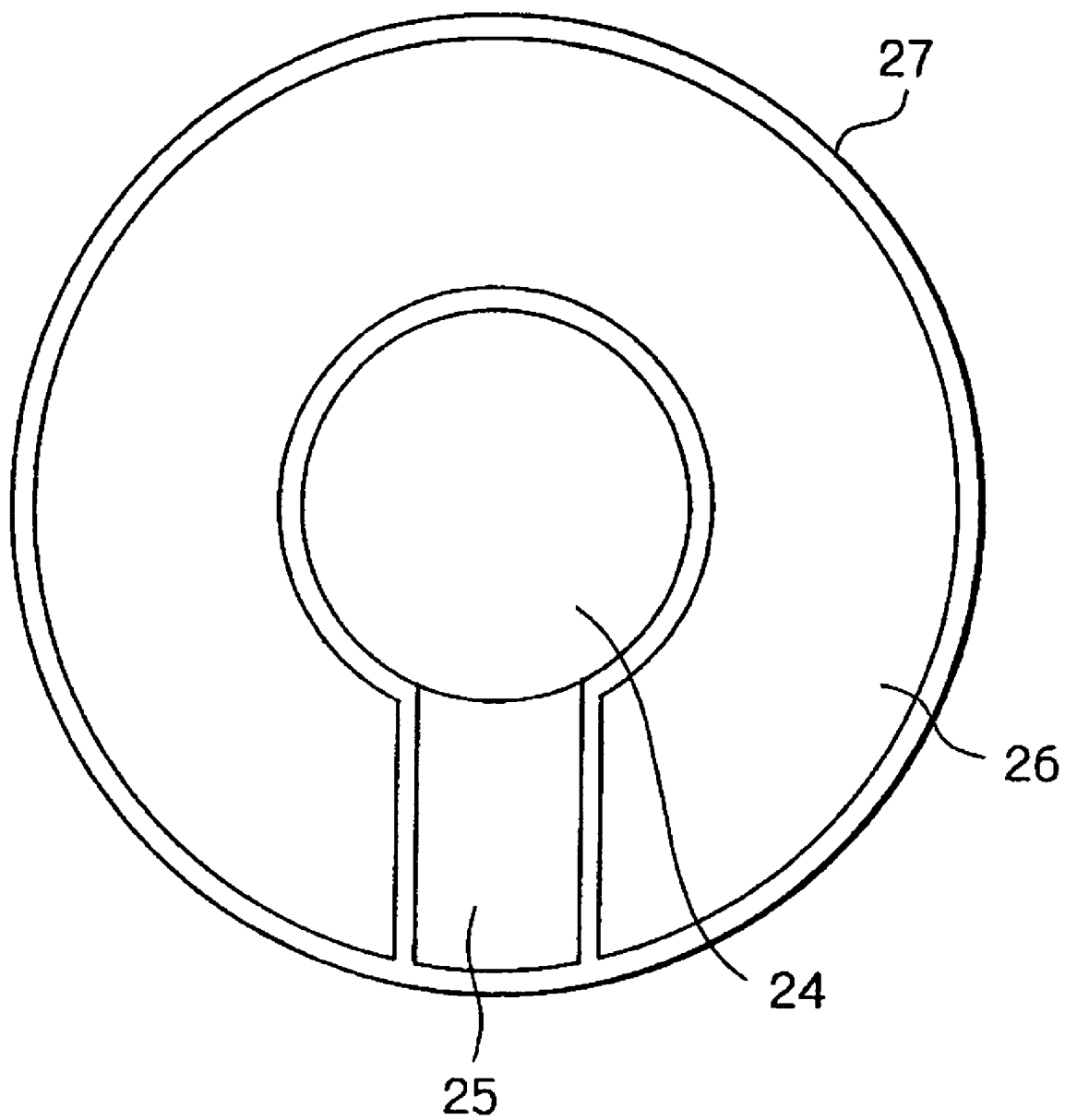
FIG. 2 is a plan view illustrating an exemplary electrostatic chuck for use in the electron beam apparatus of FIG. 1.

For electrostatically attracting and holding the wafer 15, the electron beam apparatus is provided with an electrostatic chuck 27 having an electrode plate comprised of three electrodes 24-26. In this event, for enabling even an upwardly convexly distored wafer to be held flatly, a voltage of zero volt is applied to the central electrode 24 corresponding to a central region of the electrode plate and the first electrode 25 corresponding to a portion of a peripheral region of the electrode plate, out of the three electrodes 24-26. After the voltage applied to the wafer 15 reaches −4 kV, a voltage of zero volt is applied to the second electrode 26 corresponding to the rest of the peripheral region of the electrode plate. By using the electrostatic chuck 27 in the structure illustrated in FIG. 2, even an upwardly convexly distorted wafer can be entirely flatly attracted and held by the electrostatic chuck 27.

For placing the wafer 15 on the electrostatic chuck 27, the wafer 15 is first supplied from a robot 28 to an environment chamber 29, where the wafer 15 is subjected to pre-alignment which involves rotating the wafer 15 and positioning the wafer 15 at a correct xy coordinate position. Next, after a loading chamber 30 is applied with the atmospheric pressure, a gate valve 31 is opened to introduce the wafer 15 into the loading chamber 30. Then, the gate valve 31 is closed after a loading arm is pulled out of the loading chamber 30 which is evacuated. The gate valve 32 is opened when the vacuum pressure in the loading chamber 30 reaches $1 \times 10^{-6}$ Torr or lower, and the wafer 15 is moved into the working chamber while being chucked and is placed on the electrostatic chuck having the electrodes 24-26 using the loading arm which includes the electrostatic chuck in a part thereof.

In FIG. 1, the illustrated electron beam apparatus also comprises a stage 33 for carrying the wafer 15 thereon; a valve 34; and an ion pump 35 for evacuating the column 1 through the valve 34. Preferably, the stage 33 for carrying the wafer 15 thereon is accommodated in a working chamber (not shown) made of iron, which is a ferromagnetic material, to magnetically shield the wafer 15.

The electron gun EG illustrated in FIG. 1 is operated in a space charge limited condition by sufficiently increasing a heater voltage or sufficiently extending a Wehnelt voltage. As a result, with 50 secondary electron beams detected per pixel, the evaluation such as a defect test can be sufficiently reliably carried out by the electron beam apparatus. Further, with 10 secondary electrons detected by pixel, the electron beam apparatus can be provided with a review SEM. When used as the review SEM, the stage 33 is stopped when an observation is made.

Describing next the objective lens 14, since the objective lens 14 is controlled to satisfy focusing conditions, the central electrode 19 of the objective lens 14 is applied with a previously determined fixed voltage, and the upper electrode 18 is used for dynamic focusing. This is implemented in the following procedure. The upper electrode 18 is applied with three different voltages at a position on the wafer at which patterns parallel with the x-axis and y-axis, such as dicing lines in corners of a die, exist in close proximity. At each of these voltages, pattern edges parallel with the x-direction and y-direction are scanned in the y-direction and x-direction, respectively. In this event, the slope of rising signal intensity of secondary electron beams is measured for the scanning in the y-direction and for the scanning in the x-direction, respectively. For example, assume that the signal strength rises at the slope of $a_1$ mV/μm, $a_2$ mV/μm, and $a_3$ mV/μm for the scanning in the y-direction, while the signal strength rises at the slope of $b_1$ mV/μm, $b_2$ mV/μm, and $b_3$ mV/μm for the scanning in the x-direction. From these rising slopes, maximum rising slopes a mV/μm and b mV/μm are found using a quadric approximation to the voltages applied to the upper electrode 18. Next, voltages applied to the upper electrode 18 to provide these maximum values are found to set an intermediate value of these voltages to the upper electrode 18.

When voltage differences applied to the upper electrode 18 to provide two maximum rising slopes in the x- and y-directions are larger than previously specified values, meaning that the astigmatism is large, a voltage for correcting astigmatism is preferably superposed on the electrostatic deflector 11 of the ExB separator 13.

Figure 3:
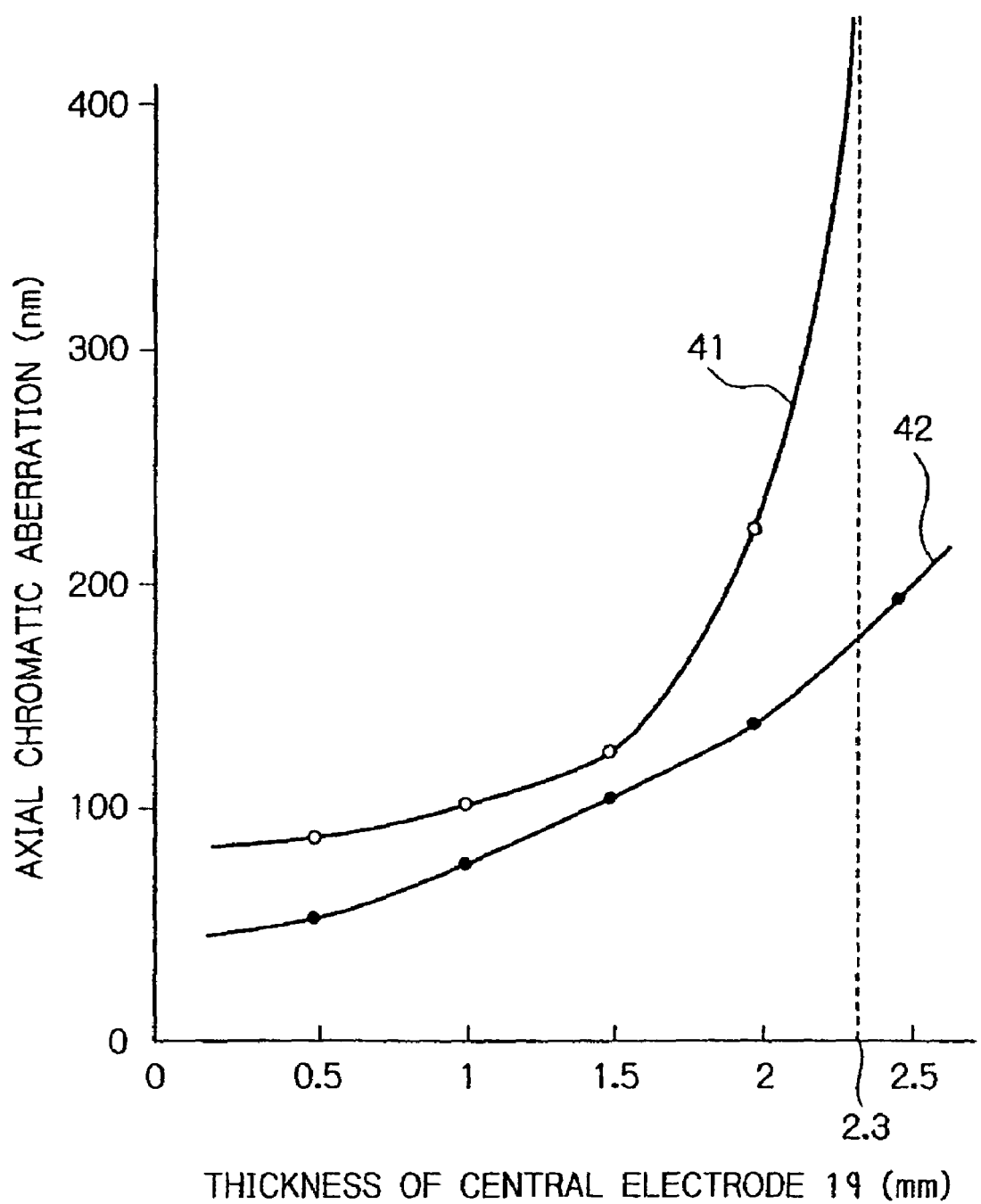
FIG. 3 is a graph showing the relationship between the thickness of a central electrode of an objective lens employed in the electron beam apparatus of FIG. 1 and axial chromatic aberration.

FIG. 3 is a graph showing a change in axial chromatic aberration when the thickness of the central electrode 19 of the objective lens 14 is changed near the optical axis, where a beam half angle on the sample surface is 30 milliradian. A difference in voltage between the upper electrode 18 and central electrode 19, and a difference in voltage between the central electrode 19 and lower electrode 20 are adjusted to be both at 20 kV or lower. In this condition, a line 41 indicates axial chromatic aberration when the lower electrode 20 is applied with a voltage which produces a filtering action for secondary electrons, and a line 42 indicates axial chromatic aberration when the lower electrode 20 is applied with a voltage which minimizes an axial chromatic aberration coefficient.

The axial chromatic aberration represents the amount of blurred beam due to an energy width. Thus, the following equation is established:

$$\Delta Cc = Cc(\Delta V/V)\alpha$$

where $\Delta Cc$ is the axial chromatic aberration, $Cc$ is the axial chromatic aberration coefficient, and $\alpha$ represents the beam half angle on the sample surface. Thus, Cc represents aberration produced per unit (energy width/beam energy) every unit beam half angle.

It can be seen in FIG. 3 that:

(1) the primary electron beam focusing condition is satisfied on condition that the lower electrode 20 is applied with a voltage which produces a filtering action on the secondary electrons only when the central electrode 19 has a thickness of 2.3 mm or less, preferably less than 2 mm;

(2) the axial chromatic aberration coefficient can be largely reduced on condition that the lower electrode 20 is applied with a voltage which produces a filtering action on the secondary electron beams when the central electrode 19 has a thickness of 1.5 mm or less; and (3) the axial chromatic aberration is reduced to 100 nm or less when the central electrode 19 has a thickness of 1.0 mm or less, and this is most preferable.

Figure 4:
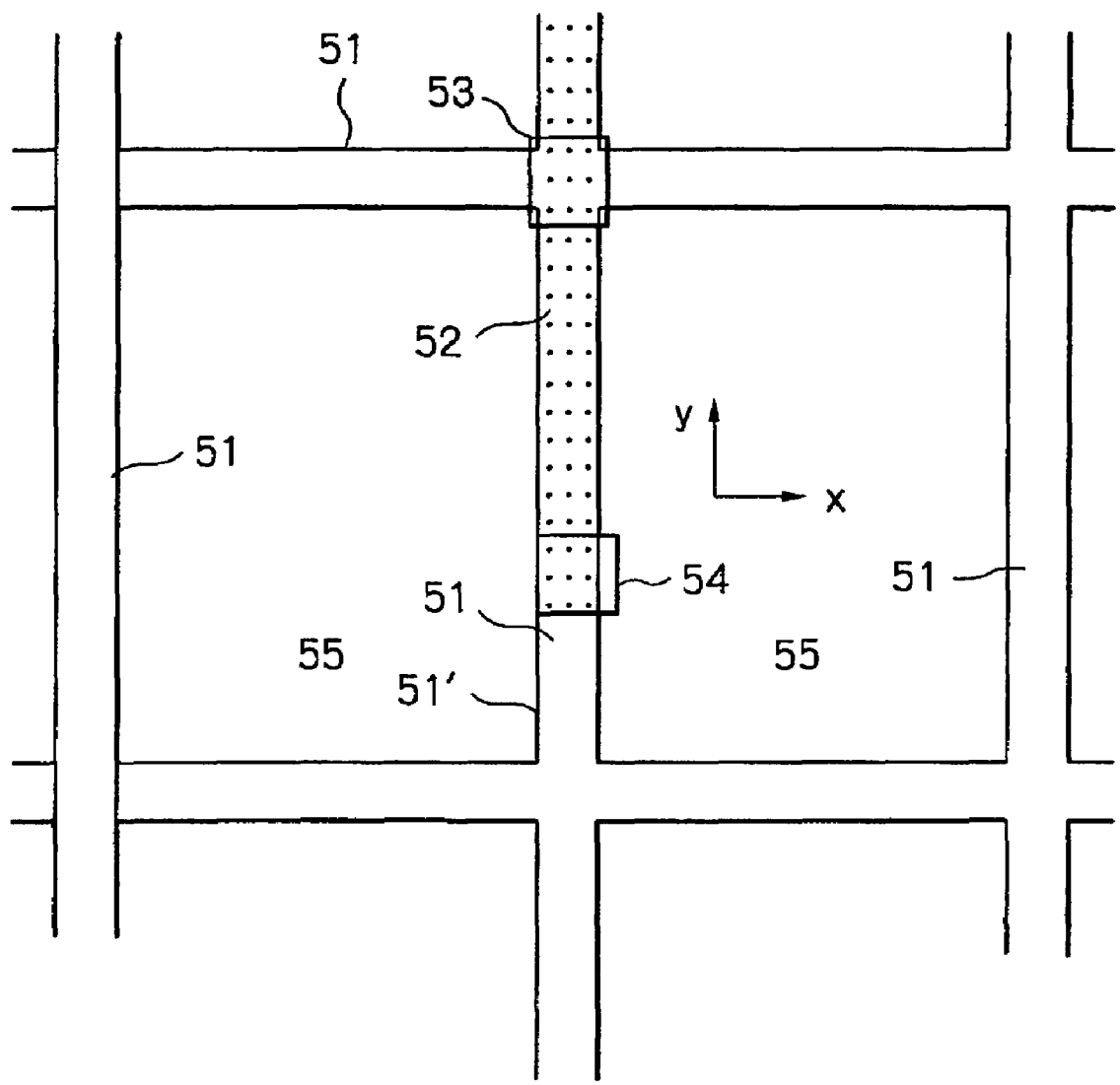
FIG. 4 is a diagram for explaining a registration method and a region under evaluation in the electron beam apparatus of FIG. 1.

FIG. 4 is a diagram for explaining an alignment mechanism for measuring a direction in which dies are arranged on the wafer 15. FIG. 4 shows dicing lines 51; one of y-direction sides 51' of each dicing line 51; a test via 52 arranged on the dicing line 51; a field of view 53 of the electro-optical system when the stage 33 is present at a first position; a field of view 54 of the electro-optical system when the stage 33 is placed at a second position after it is moved from the first position by a unit length in the y-direction; and chip areas 55.

For correcting a shift of the direction in which dies are arranged to a direction in which the stage 33 is moved in the y-direction, measurements are made on a position in the x-direction of one side 51' of one dicing line 51 extending in the y-direction within the field of view 53 of the electro-optical system, and a position in the x-direction of the side 51' within the field of view 54 of the electro-optical system. Next, the difference between these positions is divided by a unit length in the y-direction. This results in a shift angle of the direction in which the dies are arranged to the direction in which the stage 33 is moved in the y-direction. Therefore, when the stage 33 is continuously moved in the y-direction, the stage 33 may be moved in the x-direction to correct the shift angle.

In FIG. 4, the evaluation is made on the chip area 55 surrounded by adjacent dicing lines parallel with the y-axis and adjacent dicing lines parallel with the x-axis. It is noted that the chip area 55 is divided into a plurality of small regions so that those small regions do not overlap one another. Merely the small regions are evaluated. By thus defining the area under evaluation, the chip area 55 will be prevented from being irradiated twice with a beam, so that oxide films and the like of devices will not be damaged as long as the irradiation amount is held under a predetermined value.

Figure 5:
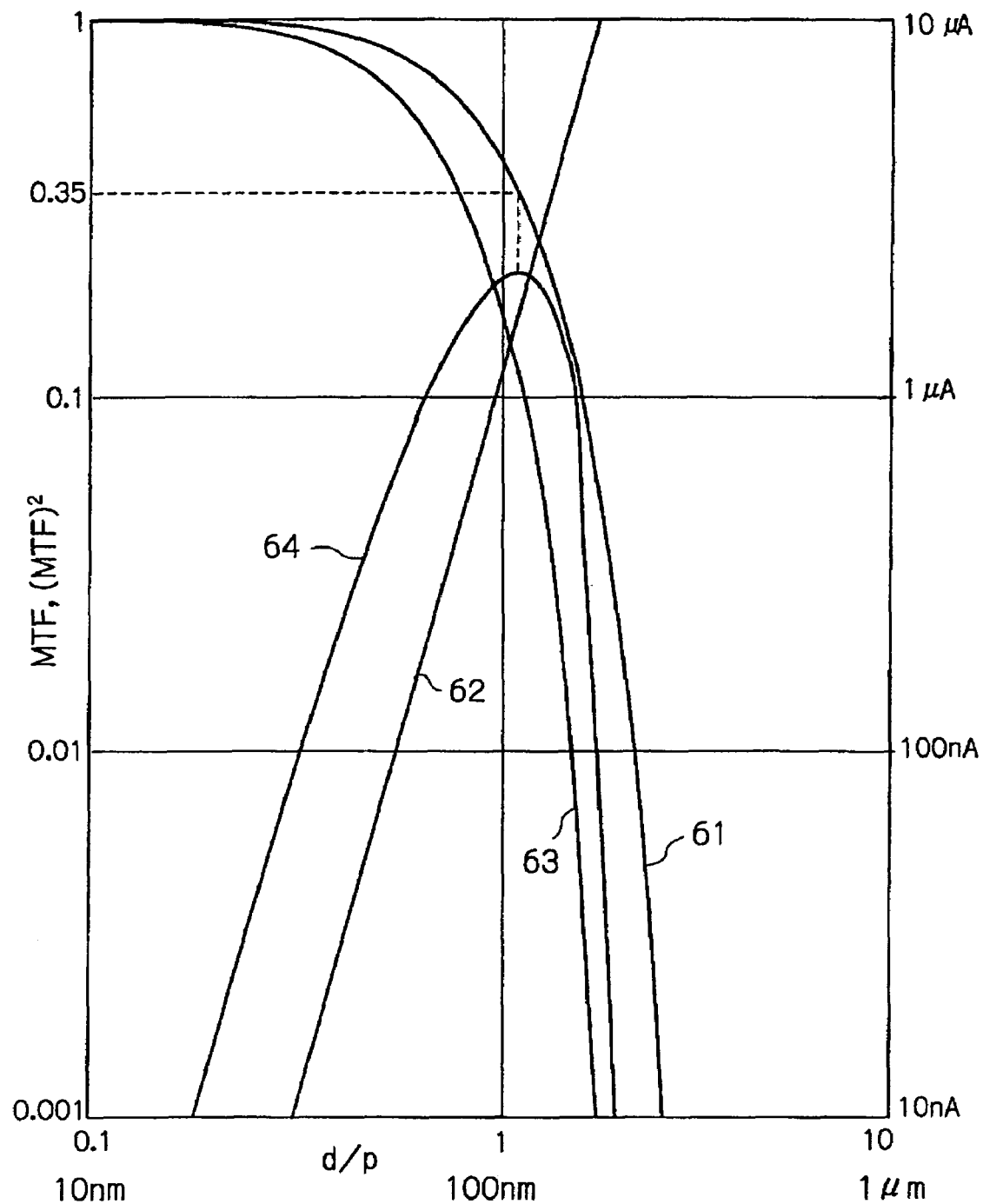
FIG. 5 is a graph showing exponential curves representing the relationship among a beam current, MTF, and S/N ratio for a beam diameter/pixel dimension in the electron beam apparatus of FIG. 1.

FIG. 5 is a graph showing a change in a variety of parameters when the horizontal axis represents d/p, where d is the dimension of the primary electron beam, and p is the dimension of a pixel. A curve 61 represents the value of MTF which shows how the contrast is reduced when the dimension d of the beam is large (i.e., when observed with a so-called blurred beam). A line 62 represents a relationship between a beam current of the primary electron beam and the diameter thereof. The beam current is proportional to the beam current to the fourth power when the axial chromatic aberration is predominant. In other words, the line 62 is a straight line increasing to the right at a slope of 4:1. A curve 63 represents a square of MFT. MFT is an acronym of Modulation Transfer Function which indicates the degree of deterioration in signal contrast when periodical structures are scanned by a blurred beam.

When shot noise is predominant, the S/N ratio of a signal output from the secondary electron detector 17 is expressed by:

$$S/N = MTF(N/2)^{1/2} \propto MTF(i)^{1/2}$$

where i is the beam current and N is the number of electrons detected per pixel. Therefore, for maximizing the S/N ratio, $(MTF)^2 i$ should be maximized. $(MTF)^2 i$ is the product of the value indicated by the line 62 and the value indicated by the curve 63, and is represented by a curve 64 which is upwardly convex. It can be seen from the curve 64 that:

(1) the S/N ratio is maximized when d/p is 1.1;

(2) the S/N ratio is substantially equal to the maximum value when $1.0 < d/p < 1.15$; and (3) the S/N ratio has a sufficiently large value when $0.9 < d/p < 1.2$.

Figure 6:
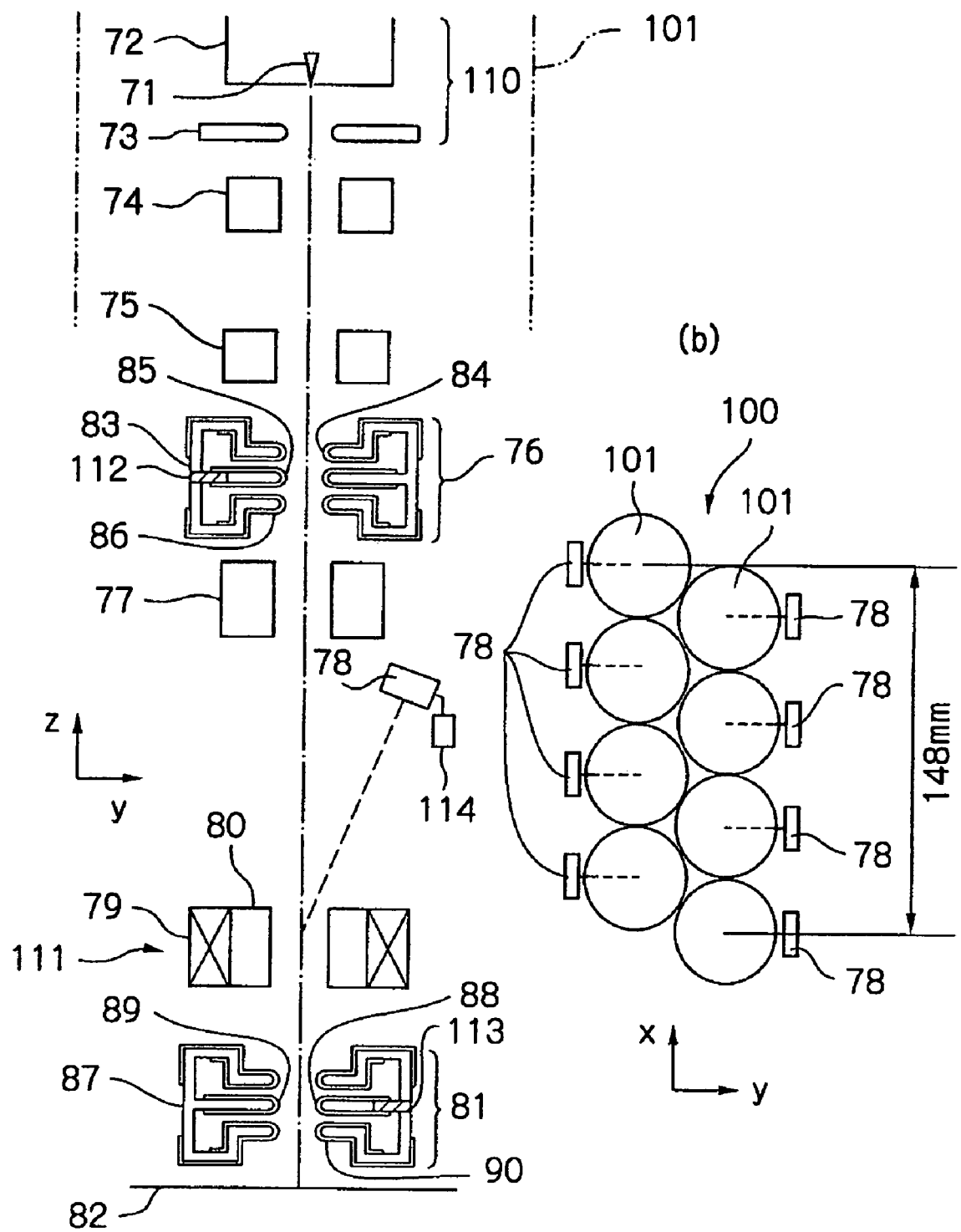
FIG. 6 is a schematic diagram generally illustrating another embodiment of the electron beam apparatus according to the present invention.

Next, a second embodiment of the electron beam apparatus according to the present invention will be described with reference to FIGS. 6 and 7. As illustrated in FIG. 6, the electron beam has a plurality (eight in the illustrated example) of electron-optical columns 100 identical in configuration, arranged side by side on a sample 82. One 101 of the electron-optical columns comprises an electron gun 110; alignment deflectors 74, 75 for aligning a primary electron beam; a condenser lens 76; an electrostatic deflector 77 for scanning the primary electron beam; an E×B separator 111 comprised of an electromagnetic deflector 79 and an electrostatic deflector 80; an objective lens 81; and detector 78 in a detection system for detecting a signal indicative of any of detected secondary electrons emitted from the sample 82, reflected electrons, or absorbed electrons.

The electron gun 110, which comprises a Wehnelt 72, a thermal electron emitting cathode 71, and an anode 73, emits the primary electron beam for irradiation to the sample 82. The thermal electron emitting cathode 71 is formed of single crystal $LaB_6$. The primary electron beam emitted from the thermal electron emitting cathode 71 of the electron gun 110 is aligned by the alignment deflectors 74, 75 with respect to the condenser lens 76, and converged by the condenser lens 76. The primary electron beam converged by the condenser lens 76 is focused on the sample 82 by the objective lens 81. Simultaneously, the primary electron beam is deflected by the static deflector 77 and the electromagnetic deflector 79 of the E×B separator 111 to scan on the surface of the sample 82. Deflection chromatic aberration is hardly produced since the deflection angle of the electromagnetic deflector 79 is set substantially twice the deflection angle of the electrostatic deflector 77.

One of secondary electrons emitted from, reflected electrons from and absorbed electrons into a scanned point on the sample 82 is accelerated and converged, as attracted by a positive high voltage applied to a central electrode 89 of the objective lens 81, separated by the E×B separator 111 from the primary optical system, introduced into a secondary optical system, and focused on the detector 78.

The detector 78 detects one of the collected secondary electrons, reflected electrons and absorbed electrons, and outputs an electric signal indicative of the magnitude thereof (signal indicative of one of the detected secondary electrons, reflected electrons and absorbed electrons) to an image forming unit, not shown. The image forming unit is also supplied with a scanning signal for deflecting the primary electron beam provided to the electrostatic deflector 77 and electromagnetic deflector 79. The image forming unit can synthesize image data from the scanning signal and electric signal to create or display an image (SEM image) representative of the scanned surface of the sample 82. Defects on the sample 82 can be detected by comparing this image data with reference image data of a sample free from defects.

As illustrated in FIG. 6, the condenser lens 76 is formed by machining a ceramic material, as a bulk insulating material, into a plurality of electrodes, and selectively applying the surfaces of the electrodes with a metal coating. The plurality of electrodes of the condenser lens 76 are comprised of an upper electrode 84, a central electrode 85, and a lower electrode 86. The central electrode 85 is applied with voltages through lead fixtures 112. Likewise, the objective lens 81 is also formed by machining a ceramic material, as a bulk insulating material, into a plurality of electrodes, and selectively applying the surfaces of the electrodes with a metal coating. The plurality of electrodes of the objective lens 81 are comprised of an upper electrode 88, a central electrode 89, and a lower electrode 90. The central electrode 89 is applied with voltages through lead fixtures 113. Since the condenser lens 76 and objective lens 81 machined in this way can be reduced in outer diameter, the electron-optical column 101 can be reduced in outer diameter, so that a larger number of electron-optical columns 101 can be arranged side by side on a single sample 82.

Next, description will be made on features in the second embodiment of the present invention. Power for heating the thermal electron emitting cathode 71 is adjusted by a current which is applied to graphite pieces (not shown) pressed on both sides of the thermal electron emitting cathode 71. The power for heating the thermal electron emitting cathode 71 is roughly adjusted, as before, to reduce an increasing rate of an emission current of the electron gun 110 when increasing the power for heating the thermal electron emitting cathode 71. Subsequently, the primary electron beam is aligned with respect to the lenses by the alignment deflectors 74, 75 and electrostatic deflector 77, and irradiated to the sample 82 as described above. A scanning voltage and a scanning current are superposed on the electrostatic deflector 77 and the electromagnetic deflector 79 of the E×B separator 111 to scan the primary electron beam on the surface of the sample 82. Then, a secondary electron signal (detected signal) generated when the primary electron beam is linearly scanned on a flat sample 82 such as bare silicon is displayed on a CRT (cathode ray tube), and an effective value of shot noise is measured by a noise meter 114. The noise meter 114 is designed to pass the secondary electron signal through a bandpass filter to rectify and smooth a noise current included in a band defined by the bandpass filter to display the effective value of shot noise.

Next, a constant beam current is caused to flow through the sample 82. Then an evaluation is made on the signal/noise ratio (S/N ratio) or noise amount when the primary electron beam is irradiated to the sample 82 while changing the power for heating the thermal electron emitting cathode 71 to determine the power for heating the thermal electron emitting cathode 71.

Figure 7:
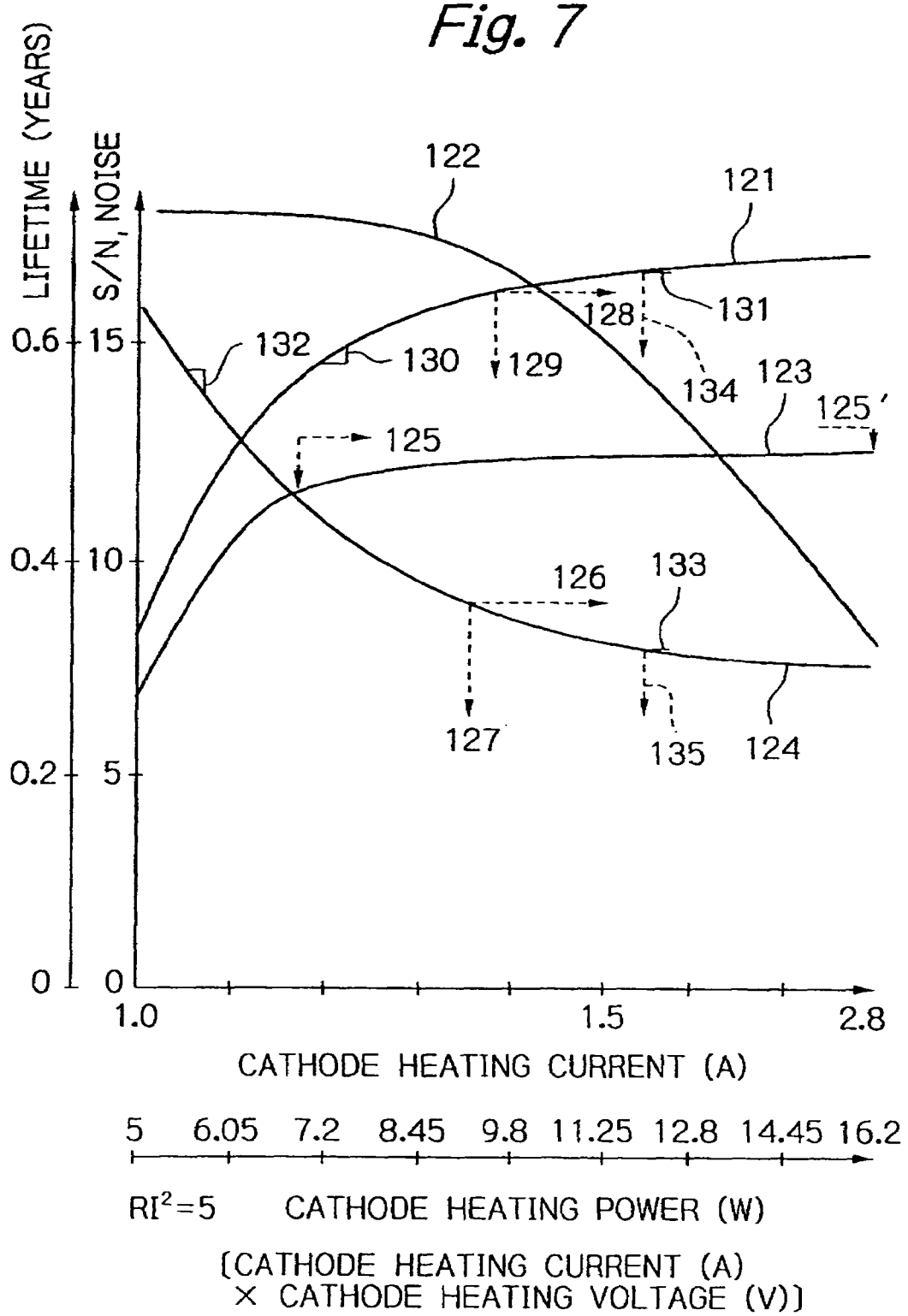
FIG. 7 is a graph showing measured values of the S/N ratio and noise amount.

FIG. 7 shows measured signal/noise ratio (S/N ratio) and noise amount in the detector 78 when a constant beam current is caused to flow through the sample 82 and the sample 82 is irradiated by the primary electron beam while changing the power for heating the thermal electron emitting cathode 71. In FIG. 7, a curve denoted by reference numeral 121 represents the S/N ratio when the thermal electron emitting cathode 71 is applied with the constant beam current. A curve denoted by reference numeral 122 represents a lifetime of the thermal electron emitting cathode 71 estimated from the relationship between the power and temperature of the thermal electron emitting cathode 71. A curve denoted by reference numeral 123 represents an emission current of the electron gun 110. A curve denoted by reference numeral 124 represents the noise amount when a constant beam current is caused to flow through the sample 82. The power for heating the electron beam emitting cathode 71 is roughly adjusted to fall within a region (from reference numeral 125 to 125') in which an electron gun current of the electron gun 110 is saturated.

As can be seen from the graph shown in FIG. 7, an increase in the power for heating the thermal electron emitting cathode 71, i.e., an increase in the temperature of the thermal electron emitting cathode 71 results in reduced shot noise (the amount of noise caused by a statistically varying number of electrons) and a higher S/N ratio associated therewith. It is therefore possible to reduce the shot noise and increase the signal/noise ratio (S/N ratio) and thus detect the secondary electrons or the like emitted from the sample with a high S/N ratio by evaluating the S/N ratio or the noise amount by the detector 78 when a constant beam current is applied to the sample from a current emitted from the thermal electron emitting cathode 71, and irradiating the sample 82 with the primary electron beam while changing the power for heating the thermal electron emitting cathode 71. Also, since the thermal electron emitting cathode 71 can be prevented from being heated to higher temperatures than necessity, the lifetime of the thermal electron emitting cathode 71 can be made longer. By provisionally setting the cathode temperature readily under the conventional condition in which the emission current is saturated, it is possible to set a condition under which the S/N ratio is increased in a relatively short time and to readily set an optimal cathode heating current. Further, an optimal cathode heating condition can be set in a short time by roughly adjusting the power for heating the thermal electron emitting cathode 71 in a conventional method, and finely adjusting the power for heating the thermal electron emitting cathode 71 by the method of the present invention described above.

Also, the power for heating the thermal electron emitting cathode 71 can be determined such that the S/N ratio exceeds a predetermined value or the noise amount is reduced to a predetermined value or less when the sample is applied with a constant beam current from an electron flow emitted from the thermal electron emitting cathode 71. For example, in FIG. 7, the power for heating the thermal electron emitting cathode 71 (product of a cathode heating current and a cathode heating voltage) is determined at a value indicated by reference numeral 129 such that the S/N ratio exceeds a value indicated by reference numeral 128. Also, the power for heating the thermal electron emitting cathode 71 is determined at a value indicated by reference numeral 127 such that the noise amount is reduced to a value indicated by reference numeral 126 or less.

Alternatively, the power for heating the thermal electron emitting cathode 71 may be determined such that an increasing rate of the S/N ratio to the heating power is reduced to a predetermined value or less, or the decreasing rate of the noise amount is reduced to a predetermined amount or less, when the sample is applied with a constant beam current from a beam emitted from the thermal electron emitting cathode 71. For example, the power for heating the thermal electron emitting cathode 71 is determined at a value indicated by reference numeral 134 such that the increasing rate of the S/N ratio to the heating power, indicated by reference numerals 130, 131, is reduced to a value indicated by reference numeral 131 or less. Also, the power for heating the thermal electron emitting cathode 71 is determined at a value indicated by reference numeral 135 such that the decreasing rate of the noise amount to the heating power, indicated by reference numerals 132, 133, is reduced to a value indicated by reference numeral 133.

In addition, the power for heating the thermal electron emitting cathode 71 may be determined by evaluating the ratio of a noise current to a beam current. Specifically, the noise current is normalized by the beam current, and the power for heating the thermal electron emitting cathode 71 may be determined such that the normalized value is reduced to a fixed value or less.

Figure 8:
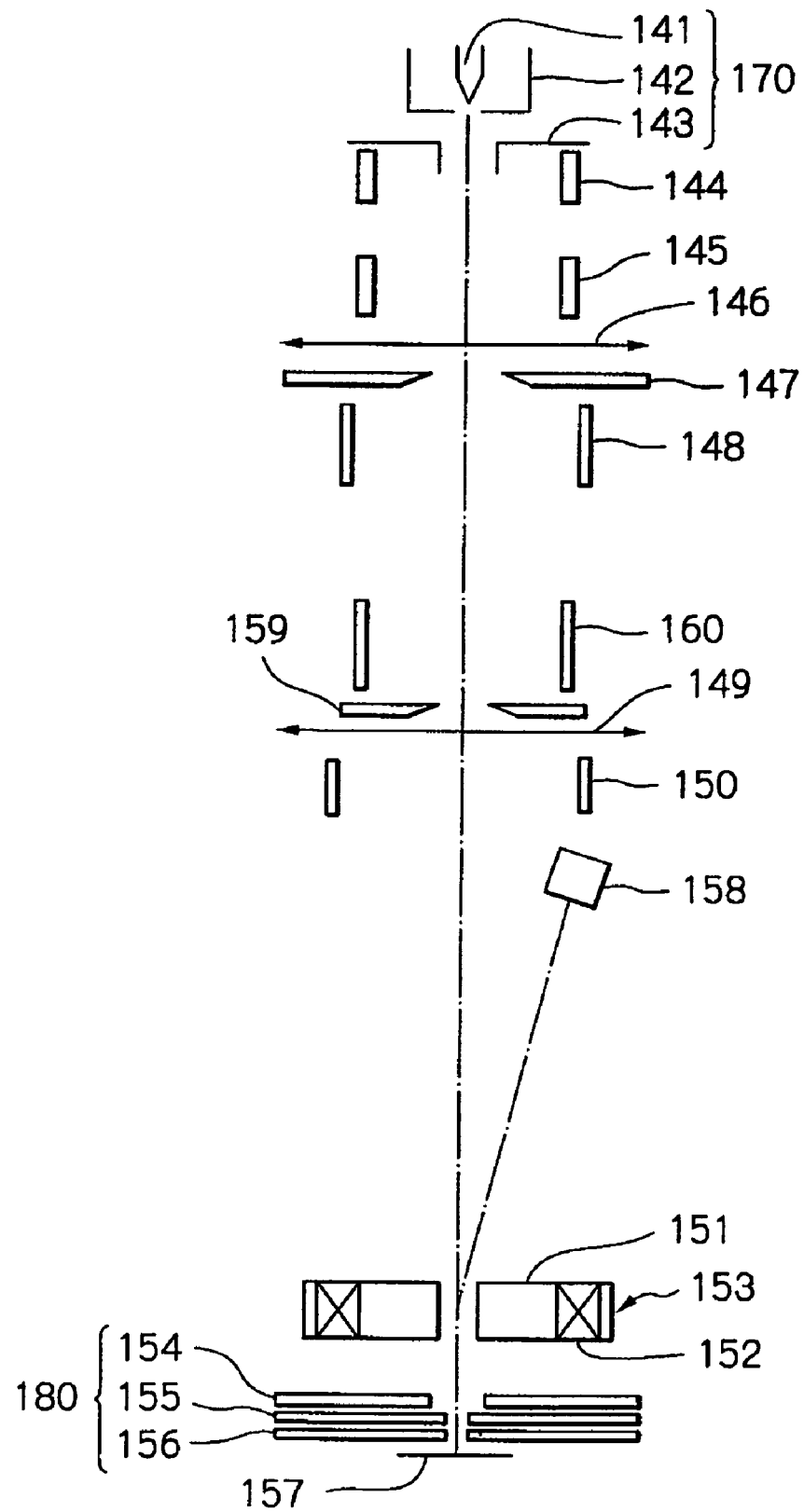
FIG. 8 is a schematic diagram generally illustrating another embodiment of the electron beam apparatus according to the present invention.

Next, a third embodiment of the electron beam apparatus according to the present invention will be described with reference to FIGS. 8 and 9. As illustrated in FIG. 8, the electron beam apparatus comprises an electron gun 170; alignment deflectors 144, 145 for aligning a primary electron beam; a condenser lens 146; an aperture 147 formed through a plate in a square shape; an NA aperture 159; a condenser lens 149; alignment deflectors 148, 160 for aligning the NA aperture 159 with condenser lens 149; an electrostatic deflector 150 for scanning the primary electron beam; an E×B separator 153 comprised of an electrostatic deflector 151 and an electromagnetic deflector 152; an objective lens 180 comprised of an upper electrode 154, a central electrode 155, and a lower electrode 156; and a secondary electron detector 158 in a detection system for detecting a signal indicative of detected secondary electrons emitted from a sample 157.

The electron gun 170, which mainly comprises a thermal electron emitting cathode 141, a Wehnelt 142, and an anode 143, emits the primary electron beam for irradiation to the sample 157. The thermal electron emitting cathode 141 is formed by polishing single crystal $LaB_6$ having the crystal orientation <100> on the surface such that the leading end thereof has a diameter of 50 µm. The Wehnelt 142 is flat and has an aperture, the diameter of which is 1.5 mm. The anode 143 has an aperture, the diameter of which is 8 mm, and is positioned 5 mm away from the Wehnelt 142 in the optical axial direction.

The primary electron beam emitted from the thermal electron emitting cathode 141 of the electron gun 170 is aligned with respect to the condenser lens 146 by the alignment deflectors 144, 145, irradiated to the aperture 147, and formed into a beam in a square shape by the aperture 147. The primary electron beam, which has passed through the aperture 147, is aligned with respect to the NA aperture 159 and condenser lens 149 by the alignment deflectors 148, 160, and converged by the condenser lens 146 to form a cross-over on the NA aperture 159. The primary electron beam, which has passed through the NA aperture 159, is converged by the condenser lens 149 (reducing lens). The primary electron beam converged by the condenser lens 149 is projected onto and focused on the sample 157 by the objective lens 180 as a reduced beam in the shape of a square having a side of 100 nm.

The sample 157 is applied with a negative voltage of −4000 V, while the lower electrode 156 of the objective lens 180 is applied with a negative voltage of −4100 V. In other words, the lower electrode 156 of the objective lens 180 is applied with a voltage lower than the negative voltage applied to the sample 157. In this way, secondary electrons emitted from a high potential pattern on the sample 157 are driven back, while secondary electrons emitted from a low potential pattern can be selectively passed through the objective lens 180, so that a potential contrast on the sample 157 can be provided with a high S/N ratio.

Since the central electrode 155 of the objective lens 180 is applied with a voltage of 20 KV, secondary electrons emitted from a scanned point on the sample 157 are accelerated (by an electric field generated by the objective lens 180) and converged, as attracted by the positive high voltage applied to the central electrode 155 of the objective lens 180, in a normal operation, separated from the primary optical system by the ExB separator 153, and collected to the secondary electron detector 158. The ExB separator 153 is made up of an octapole electrostatic deflector 151 wound with a saddle-shaped deflector on the outer periphery, and a core formed of a permalloy on the outside of the deflector.

The sample 157 is scanned through two-stage deflection by the electrostatic deflector 150 and the electrostatic deflector 151 of the ExB separator 153. In this event, the two deflectors have deflection pivot at positions which minimize deflection chromatic aberration near the objective lens 180. More specifically, the deflection pivots of the two deflectors are set slightly above the upper electrode 154 of the objective lens 180, thereby minimizing the deflection chromatic aberration at the time when the electron beam passes through the objective lens 180.

The detector 158 detects the collected secondary electrons and outputs an electric signal indicative of the magnitude thereof (signal indicative of the detected secondary electrons) to an image forming unit, not shown. The image forming unit is also supplied with a scanning signal for deflecting the primary electron beam provided to the electrostatic deflector 150 and electrostatic deflector 151. The image forming unit can synthesize image data from the scanning signal and electric signal to create or display an image (SEM image) representative of the scanned surface of the sample 157. Defects on the sample 157 can be detected by comparing this image data with reference image data of a sample free from defects.

A plurality of electrodes of the ExB separator 153 are formed by machining a machinable ceramic material into electrodes and selectively applying the surfaces of the electrodes with a metal coating, so that the outer diameter can be reduced. Since the electromagnetic deflector 152 is a saddle-shaped deflector, it can also be reduced in outer diameter. The ExB separator 153 can be formed to have the outer diameter of approximately 40 mm, making the outer diameter small. If 12 electron-optical columns are arranged in this manner on a single sample 157, the resulting throughput can be increased by a factor of 12.

Figure 9:
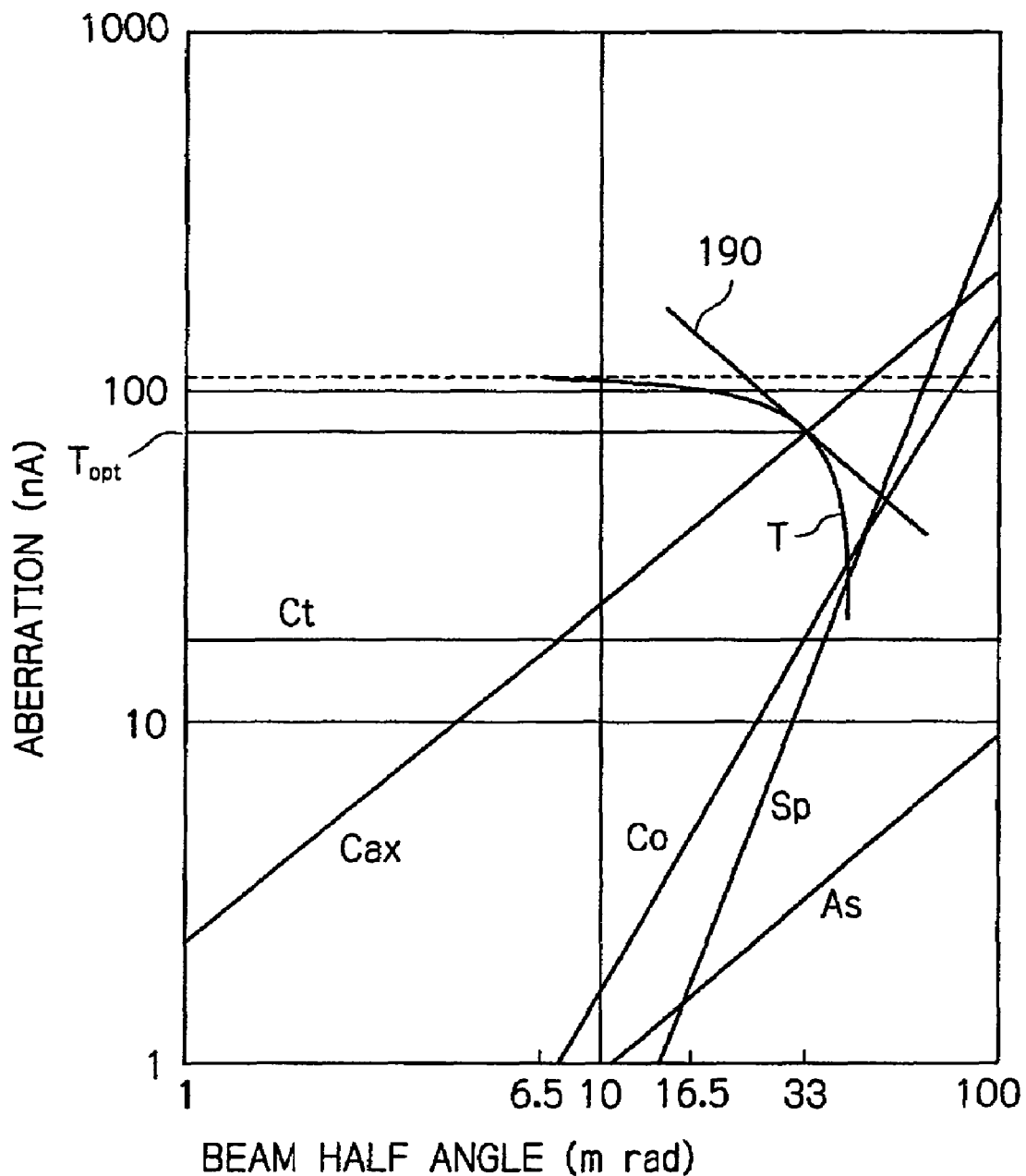
FIG. 9 is a graph for calculating a beam current generated in an optical system in the embodiment of FIG. 8.

As described above, a beam current of 20 nA or more can be provided with a beam having a diameter of 110 nm by minimizing the deflection chromatic aberration when the beam passes through the objective lens 180. The following description will be focused on this feature in specific manner. FIG. 9 is a graph which shows a beam current generated in the optical system, which is calculated when the distance between the lower electrode 158 of the objective lens 180 and the sample 157 is set to 2 mm in the optical axial direction. In FIG. 9, Ct indicates the deflection chromatic aberration; Cax, axial chromatic aberration; Co, coma aberration; Sp, spherical aberration; and As, astigmatism. T indicates a diameter reduced on the sample 157 of the aperture 147 for providing a beam having a diameter of 110 nm, and can be calculated by:

$$T^2 = 110^2 - Ct^2 - Cax^2 - Co^2 - Sp^2 - As^2$$

and appears to be a curve as shown in FIG. 9. A straight line 190 is inclined downward to the right at an angle of 45 degrees, and a tangential point of the straight line 190 with the curve T indicates an optimal value. Specifically, the aperture half angle is 33 mrad, Topt is 76.4 nm, and the beam current I is calculated by:

$$\begin{aligned} I &= \pi^2 (33 \times 10^{-3})^2 \times (76.4 \times 10^{-5}/2)^2 \times 1.5 \times 10^5 \\ &= (\pi \times 1.26 \times 10^{-5} \times 1 \times 10^{-2})^2 \times 1.5 \times 10^5 \\ &= 23.5 \text{ nA} \end{aligned}$$

It will be understood from the foregoing that a beam current of 20 nA or more can be provided. This calculation is applied when a cross-over image is reduced for use as a probe. A larger beam current can be provided when a reduced image of electron beams passing through an aperture is used as a probe.

The electron gun 170 can be operated under a space charge limited condition. In this event, shot noise $I_N$ is calculated as follows, assuming that the transmissivity of secondary electrons is 50%:

$$\begin{aligned} I_N &= \Gamma \times (2eI\Delta f)^{1/2} \text{ (where } \Gamma = 0.13) \\ &= 0.13 \times (2 \times 1.6 \times 10^{-19} \times 10 \times 10^{-19} \times 100 \times 10^6)^{1/2} \\ &= 7.35 \times 10^{-11} \text{ A} \end{aligned}$$

Therefore, the S/N ratio is calculated as follows:

$$S/N = 10 \times 10^{-9}/7.35 \times 10^{-11} = 136$$

Thus, the electron beam apparatus in the third embodiment can reduce the shot noise, satisfy the S/N ratio higher than 45, required for conducting a defect test and the like, eliminate the need for scanning twice or four times for average summation, generate a sufficient signal in a single scanning session even when it operates at frequency of 100 MHz or higher, and provide a beam for ensuring a resolution of 100 nm with the S/N ratio higher than 45.

Now, a method of manufacturing semiconductor devices according to the present invention will be described with reference to FIGS. 10 and 11. The method of manufacturing semiconductor device according to the present invention involves an evaluation on a wafer in the middle of the process or on a finished wafer using the electron beam apparatus described above. In the following, a general method of manufacturing semiconductor devices will be described with reference to flow charts of FIGS. 10 and 11.

Figure 10:
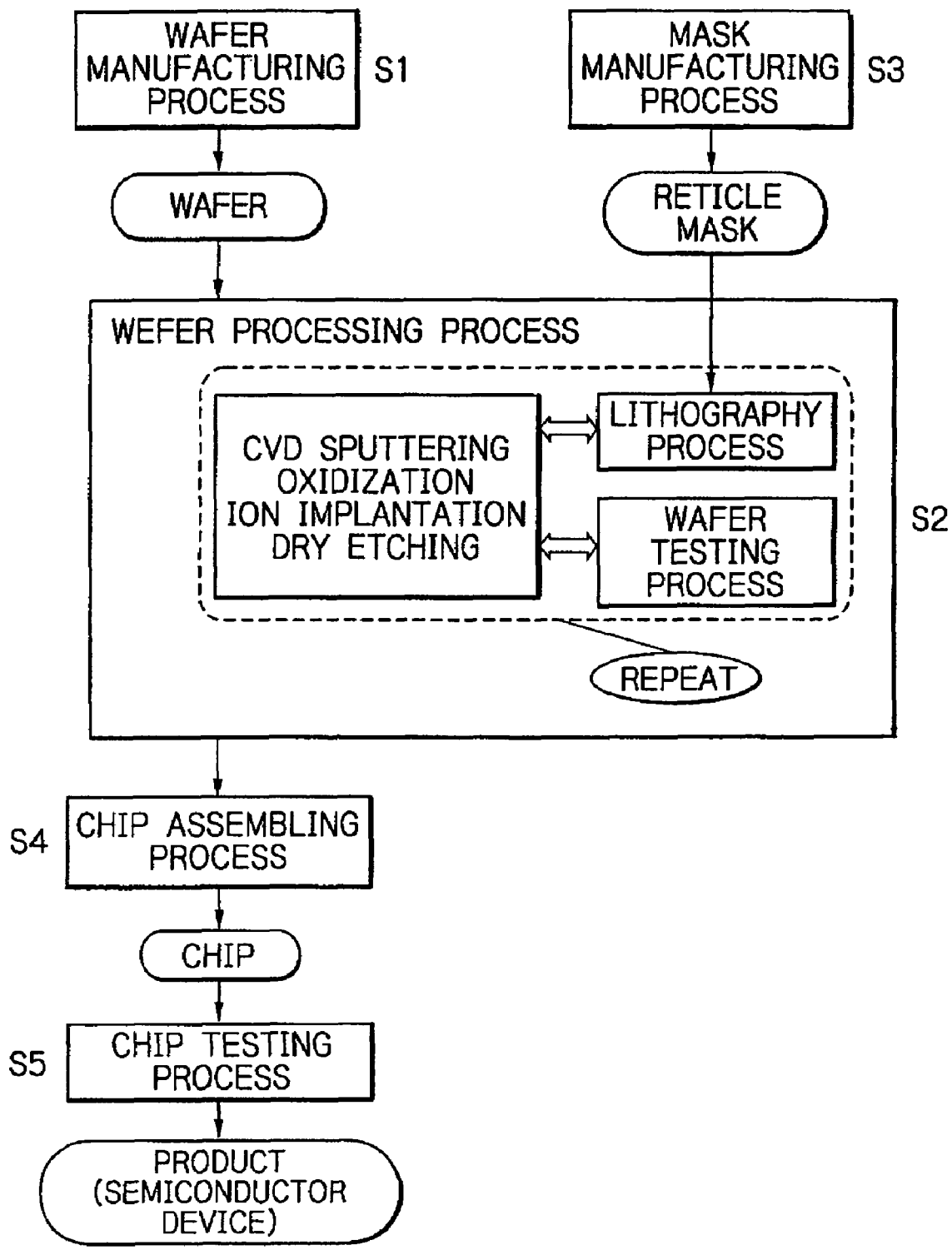
FIG. 10 is a flow chart illustrating a method of manufacturing semiconductor devices, applying the electron beam apparatus according to the present invention.

As illustrated in FIG. 10, the semiconductor device manufacturing method is generally divided into a wafer manufacturing process S1 for manufacturing wafers; a wafer processing process S2 for processing the wafers as required; a mask manufacturing process S3 for manufacturing masks required for exposure; a chip assembling process S4 for singulating individual chips formed on a wafer and making them operable; and a chip testing process S5 for testing finished chips. Each of these processes includes several sub-processes.

In the foregoing processes, the wafer processing process exerts a deterministic influence on the manufacturing of semiconductor devices. This is because the wafer processing process involves the formation of designed circuit patterns on a wafer and the formation of a large number of chips which operate as memories or MPU.

It is therefore important to evaluate how a wafer is processed in a sub-process of the wafer processing process which affects the manufacturing of semiconductor devices. This sub-process will be described below.

First, a dielectric film is formed to serve as an insulating layer, and a metal thin film is formed for creating wires and electrodes. The thin film is formed by CVD, sputtering, or the like. Next, the formed dielectric thin film, metal thin film, and wafer substrate are oxidized, and a resist pattern is formed in a lithography process using a mask or a reticle created in the mask manufacturing process S3. Then, the substrate is machined commensurate with the resist pattern by a dry etching technique or the like, and is implanted with ions and impurities. Subsequently, the resist layer is peeled off for testing the wafer.

The wafer processing process as described above is repeated as many times as a required number of layers, and the wafer before separated into chips is formed in the chip assembling process S4.

Figure 11:
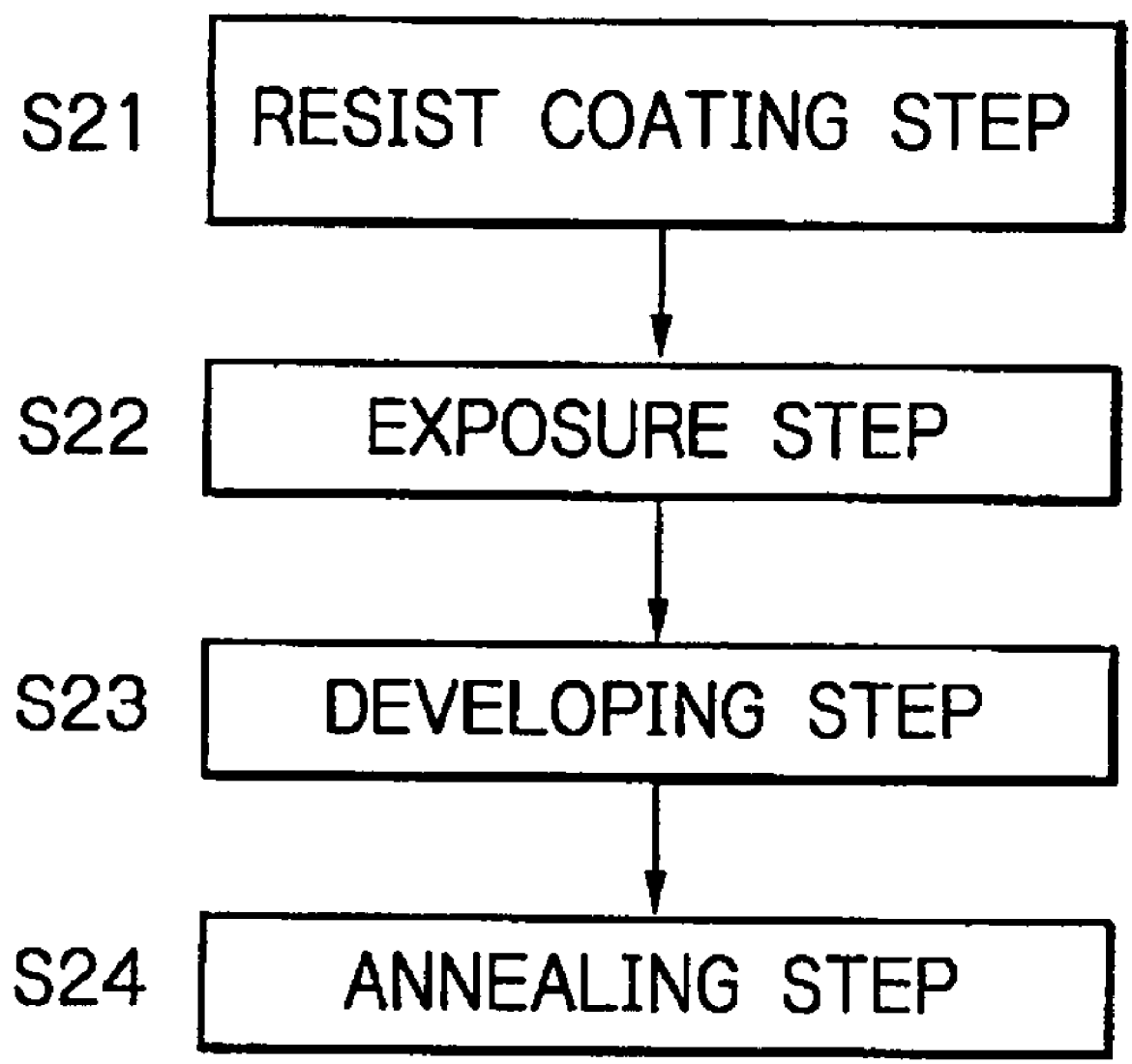
FIG. 11 is a flow chart illustrating a lithography process which is a sub-process of a wafer processing process shown in FIG. 10.

FIG. 11 is a flow chart illustrating the lithography process which is a sub-process of the wafer processing process in FIG. 10. As illustrated in FIG. 11, the lithography process includes a resist coating step S21, an exposure step S22, a developing step S23, and an annealing step S24.

In the resist coating step S21, a resist is coated on the wafer formed with circuit patterns using CVD or sputtering, and the coated resist is exposed in the exposure step S22. Then, the exposed resist is developed to create a resist pattern in the developing step S23, and the developed resist pattern is annealed for stabilization in the annealing step S24. These steps S21-S24 are repeated as many times as a required number of layers.

In the semiconductor device manufacturing method of the present invention, defects on a wafer can be detected without fail even in semiconductor devices having ultra-thin patterns, using the electron beam apparatus described in connection with FIGS. 1 to 9, which can provide images with reduced distortions and blurs, in the chip testing process S5 for testing finished chips. It should be noted that the electron beam apparatus may be installed near any processing apparatus as long as it involves processing which requires evaluations.

What is claimed is:

1. An electron beam apparatus having an electro-optical column for illuminating a sample by an electron beam emitted from a thermal electron emitting cathode to detect any one of a secondary electron, a reflected electron and an absorbed electron, wherein a signal/noise ratio or an amount of noise in detecting means is estimated when the sample is illuminated by the electron beam while electric power for heating the cathode is changed to determine a value of the electric power for heating the cathode.

2. An electron beam apparatus as claimed in claim 1, wherein a value of electric power for heating the cathode is determined so that the signal/noise ratio is above a predetermined value when a constant beam current flows from the electron beam emitted from the cathode to the sample.

3. An electron beam apparatus as claimed in claim 1, wherein a value of electric power for heating the cathode is determined so that a ratio of increase in a value of electric power for heating the cathode to the signal/noise ratio is equal to or smaller than a predetermined value or that a ratio of decrease in the amount of noise is equal to or smaller than a predetermined value when a constant beam current flows from the electron beam emitted from the cathode to the sample.

4. An electron beam apparatus as claimed in claim 1, wherein a value of electric power for heating the cathode is determined by estimating a ratio of a noise current to a constant beam current when the constant beam current flows from the electron beam emitted from the cathode to the sample.

5. An electron beam apparatus as claimed in claim 1, wherein a value of the heating electric power is tentatively determined so that an electron gun current is changed slowly when electron power for heating the cathode is changed, and wherein, after the determination, a value of electric power for heating the cathode is determined on the basis of an estimate of a signal/noise ratio or an amount of noise in the detecting means.

6. An electron beam apparatus as claimed in claim 1, wherein a value of electric power for heating the cathode is determined taking into consideration a relation between electric power for heating the cathode and the signal/noise ratio and a relation between electric power for heating the cathode and a lifetime of the cathode.

7. A method of manufacturing a device using an electron beam device as claimed in any one of claims 1-6 to estimate a wafer being worked or a finished wafer.

* * * * *